United States Patent
Troschl

(10) Patent No.: US 11,951,074 B2
(45) Date of Patent: Apr. 9, 2024

(54) DEVICE FOR FILLING BLOOD PRODUCTS

(71) Applicant: on point medicals GmbH, Klagenfurt (AT)

(72) Inventor: Clemens Troschl, St. Veit an der Glan (AT)

(73) Assignee: on point medicals GmbH, Klagenfurt (AT)

( * ) Notice: Subject to any disclaimer, the term of this patent is extended or adjusted under 35 U.S.C. 154(b) by 323 days.

(21) Appl. No.: 17/187,722

(22) Filed: Feb. 26, 2021

(65) Prior Publication Data

US 2021/0283015 A1    Sep. 16, 2021

(30) Foreign Application Priority Data

Mar. 10, 2020   (DE) .................... 10 2020 106 451.9

(51) Int. Cl.
| | |
|---|---|
| *A61J 1/20* | (2006.01) |
| *B65B 3/00* | (2006.01) |
| *A61F 9/00* | (2006.01) |
| *A61J 1/10* | (2006.01) |

(52) U.S. Cl.
CPC .......... *A61J 1/2048* (2015.05); *A61J 1/2068* (2015.05); *A61J 1/2079* (2015.05); *A61J 1/2082* (2015.05); *B65B 3/003* (2013.01); *A61F 9/0008* (2013.01); *A61J 1/10* (2013.01)

(58) Field of Classification Search
CPC .......... A61J 1/2068–2075; A61J 1/2082; A61J 1/05; A61J 1/06; A61J 1/062; A61J 1/065; A61J 1/067; A61J 1/10; A61J 1/12; B65B 3/04; B65B 3/003
See application file for complete search history.

(56) References Cited

U.S. PATENT DOCUMENTS

| | | |
|---|---|---|
| 3,405,706 A | 10/1968 | Cinqualbre |
| 3,566,930 A | 3/1971 | Kirschner |
| 5,279,576 A * | 1/1994 | Loo ........................ A61J 1/2096 222/1 |
| 5,507,299 A | 4/1996 | Roland |
| 2003/0230521 A1 | 12/2003 | Schick |
| 2004/0127816 A1 | 7/2004 | Galvao |
| 2007/0186992 A1* | 8/2007 | Bullen ..................... B65B 3/003 141/65 |
| 2013/0220484 A1* | 8/2013 | De Marco ............. A61J 1/2037 141/183 |

(Continued)

FOREIGN PATENT DOCUMENTS

| | | |
|---|---|---|
| DE | 202011004487 | 6/2012 |
| WO | WO 2014/108852 | 7/2014 |

*Primary Examiner* — Leslie Lopez
*Assistant Examiner* — Seth Han
(74) *Attorney, Agent, or Firm* — McDonnell Boehnen Hulbert & Berghoff LLP

(57) ABSTRACT

Device (1) for filling blood products (12) into at least two administration containers (2), comprising at least one receptacle (3) for dispensing the blood product (12) into the device (1), a channel system (4, 7, 8, 17) connected to carry fluid to the administration containers (2), and an air exhaust assembly (10, 11, 15), where the device (1) further comprises a plate-shaped component (6) in which the channels (7, 8, 17) of the channel system run, through which the administration containers (2) can be filled in parallel with equal volumes of the blood product (12).

11 Claims, 3 Drawing Sheets

(56) References Cited

U.S. PATENT DOCUMENTS

Figure 1:
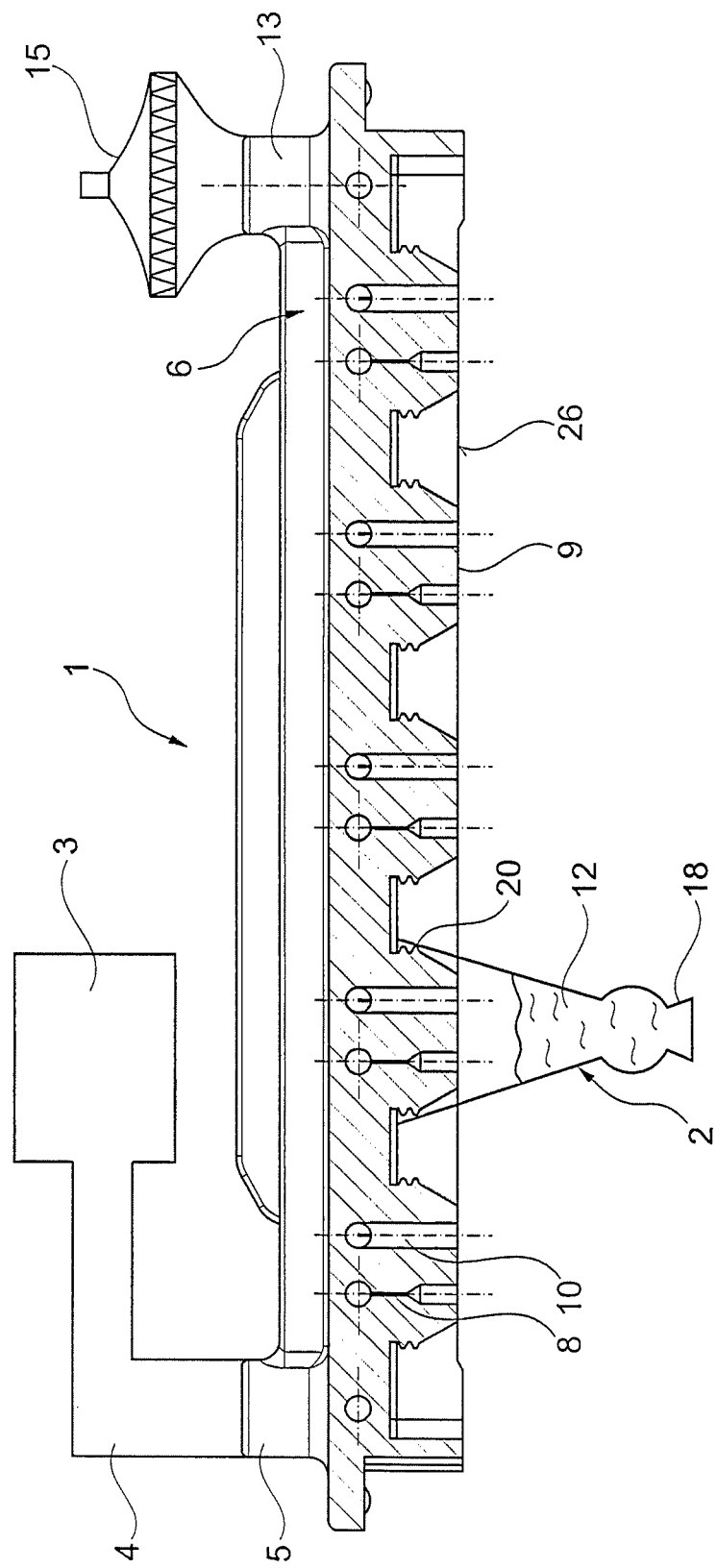

2019/0106312 A1* 4/2019 Semmler ............... B67C 3/286
2019/0241287 A1 8/2019 Goodwin et al.
2019/0276174 A1* 9/2019 Gschwendtner ...... B29C 66/849

* cited by examiner

DEVICE FOR FILLING BLOOD PRODUCTS

CROSS REFERENCE TO RELATED APPLICATION

This application claims the benefit of German Patent Application No. 10 2020 106 451.9, filed Mar. 10, 2020, which is hereby incorporated by reference in its entirety.

The disclosure concerns a device for filling blood products, in particular serum eye drops, as described in the overview in claim 1.

Blood products such as serum or platelet-rich plasma are needed for special treatment methods. These blood products can be autologous or allogenic. Autologous means that these products were taken from the patient's own blood, while allogenic blood products are taken from unrelated donors. In recent years, the demand for serum eye drops in particular has increased, because they promote the healing of the cornea in known types of severe eye disease. In order to fill these blood products into smaller containers, such as eye drop bottles, according to GMP (good manufacturing practice) guidelines, the strictest clean room requirements are necessary in order to prevent contamination and guarantee safety.

Safe filling of blood products outside of a clean room requires a closed device, which is delivered to the user (blood bank or hospital) empty and in sterile packaging. On site, the blood product is then filled into the device by technically trained staff, sealed, and packaged in administration containers for patients.

Similar closed devices with administration containers for filling blood products are disclosed in DE202011004487 U1 or WO 2014/108852 A1.

These devices are used to manufacture, store, transport, and apply finished measured doses, ready for use directly in patients, of own-serum eye drops or other drugs made from blood or blood products without the need for clean room laboratories.

The administration containers used in them are connected to each other by multiple tubes. In addition, each administration container has a dropper outlet. This makes production of these devices extremely time- and cost-intensive, because the tubes as well as the dropper outlets are attached manually.

For both devices, each administration container must be individually removed, which makes manufacturing the blood product equally time-intensive.

The goal of the disclosure presented here is therefore to improve upon a device of the aforementioned type so that the device can be manufactured economically. In addition, the disclosure is intended to radically shorten the time required to fill multiple administration containers with a given blood product and to make the laboratory worker's job significantly easier. Also, patients should benefit from a container that is specifically designed for use in the eyes (for the case of filling serum eye drops).

The disclosure achieves the goal through the features in the independent patent claims, while advantageous embodiments and examples of the disclosure can be found in the subordinate claims.

One advantageous feature is that the device includes a plate-shaped component with the channels of a channel system running through it, and through those channels the administration containers can be filled in parallel with identical amounts of the blood product.

This disclosure therefore concerns a device for uniform distribution and filling of blood products (e.g., autologous serum eye drops or platelet-rich plasma) into small containers, preferably administration containers. These administration containers have a capacity of 1.5 ml or 5 ml, for example.

The device consists of a plate-shaped component, which has connections for the administration containers, a connection (inlet) for the liquid blood product, and a connection (outlet) for air exhaust. For this disclosure, such a plate-shaped component can be in the form of a round disk, a rectangular plate, or a flat polyhedron, as long as it is completely flat.

All connectors for the administration containers on the underside of the plate-shaped component have a supply channel and an air exhaust channel. The plate-shaped component is therefore characterized in that the supply channels are arranged in the component such that all containers can be filled in parallel and uniformly.

Consequently, the disclosure includes a device for filling blood products that allows the administration containers to be filled in such a way that all administration containers are filled simultaneously and uniformly.

The component has a plate-like shape and consists of either a single base plate or a baseplate combined with at least one cover plate, so that the at least one cover plate is attached solidly to the base plate. This is achieved, for example, by a bonding technique wherein the plates are pressed onto each other using heat and pressure. The cover plate can also take the form of a film.

The base plate—in the single design or in combination with at least one cover plate—has multiple connectors for the administration containers on its underside. The connectors are cone-shaped for easier attachment of the administration containers. They have cutting edges to guarantee a stable and sealed connection. The administration containers can be commercially available eye drop applicators, for example. The device can perform its function only if all administration containers are closed and the plate-shaped component is horizontally aligned, with the administration containers on the underside.

The plate-shaped component has a connector for attaching a receptacle with the blood product through a tube. Therefore, for example, a defined volume of the blood product can be pulled through a syringe and filled into the containers through a valve and using the channel arrangement in the plate-shaped component. The serum can be provided in a bag. To make filling possible, the component has an outlet for air exhaust, to allow the air in the channels and containers to escape. A sterile filter is attached to this air exhaust outlet for compliance with the GMP requirements.

Inside the component, a channel runs from the connection for the blood product and splits into additional channels in order to fill all of the administration containers attached to the connectors. The channels are arranged so that all containers can be filled simultaneously and uniformly. This can be accomplished, for example, by means of a change in the cross-section of the connectors. This cross-section change results in a higher pressure of the fluid before the cross-section change and acceleration of the fluid at the cross-section change (nozzle effect). The higher, uniform pressure before all connectors leads to simultaneous filling of all administration containers.

All connectors have an air exhaust channel, and the air exhaust channels are directed together to the air exhaust outlet, which has a connector for a filter. This filter is a typical commercial sterile filter, for example, with a pore size of 0.22 µm.

For the filling process, for example, a syringe is located between the serum bag and the plate-shaped component in the supply line. With the syringe, a defined volume of around 30-50 ml can be drawn in, wherein the syringe has a special commercially available valve so that it functions like a pump, pulling the fluid in on one side of the valve and then pushing it out on the other side of the valve.

An additional embodiment consists of using a peristaltic pump connected to the bag to control the inflow of the blood product.

An additional embodiment consists of using a press connected to the bag to control the inflow of the blood product.

An additional embodiment consists of using a vacuum to evacuate the container and then allowing the fluid to flow in through a valve.

A mechanical device is also conceivable for carrying the blood product into the plate-shaped component.

For assembly, before the administration containers are attached to the connectors on the base plate, the administration containers are arranged on a support surface matching the distribution of the connectors. In support, a holding frame can be used here to arrange the containers correctly, e.g., in a grid pattern.

The base plate is then rotated, and the connectors are inserted into the administration containers, which are open at the top and are arranged on the support surface in positions matching the connectors.

In another embodiment, for assembly the base plate is placed upside down on a support surface, and the administration containers, which can be transported using the holding frame, are attached to the connectors. The administration containers, sterile filter, and connector are assembled in a clean room. The product is then packaged and sterilized and can be delivered to the user (blood bank or hospital).

After the filling process, the administration containers are sealed and removed at the upper end near the component.

To remove the administration containers from the connectors on the plate-shaped component, the following methods are possible, for example:
  Cut-off sealing, e.g., with pressure-cutting tools such as snips
  Thermo-sealing with pre-determined tearing lines
  Freezing of the ends on either side of the separation location before removal
  Ultrasonic sealing An advantageous feature of the disclosure is that multiple administration containers can be removed in one sealing and removal process.

Suitable materials for the invented device's plate-shaped component are, for example, polyvinyl chloride (PVC), polyurethane (PU, PUR), polyethylene (PE), polypropylene (PP), or polystyrene (PS). The component is preferably produced as an injection molded part in a clean room atmosphere.

The figures show:
  FIG. 1: Side view of the device
  FIG. 2: View from below of the plate-shaped component
  FIG. 3: View from above of the plate-shaped component
  FIG. 4: Perspective view of the administration containers
  FIG. 5: Schematic representation of the channel pathways FIG. 1 shows how, exiting from a receptacle 3, the blood product or blood serum is directed through a feed line 4 to the plate-shaped component 6.

The receptacle 3 can be, for example, a syringe attached to the feed line 4, which can be a piece of tubing, for example. The other end of the feed line 4 is connected to the connection 5 of the plate-shaped component 6.

FIG. 1 shows a side view of the plate-shaped component 6, and in this embodiment there is no separate cover plate covering the component from above and the lower part of the plate-shaped component 6 is shown in cross-section. The component 6 has multiple connectors 9, which are molded on the underside 26 of the plate-shaped component. A supply channel 7, not visible, which runs horizontally inside the component 6, carries the blood product introduced through a connection 5 to the visible vertical channel 8, which takes the blood product to the individual connectors 9 and distributes it uniformly.

The supply channel 7 runs lengthwise through the plate-shaped component 6 and branches off concentrically from a connector 9 to form a supply channel 8 running perpendicular to the supply channel 7. This perpendicular supply channel 8 can have a cross-sectional constriction, in order to guarantee uniform filling. According to FIG. 1, five supply channels 8 are available, each of which can fill one administration container 2 attached to a connector 9 with the liquid blood product 12.

Preferably, a connector 9 has a conical shape, to facilitate the attachment of an administration container. Cutting edges 20 can be attached to the connectors 9, in order to guarantee a stable and sealed connection with the attached administration container 2.

In addition to a supply channel 8, each connector 9 is connected to an air exhaust channel 10, through which the air introduced into the administration containers 2 and channels from the inflowing fluid stream during the filling process can be exhausted. The air exhaust channels 10 guide the air to the central air exhaust channel 11 (not visible), which carries it in the direction of the connection 13.

The connection 13 has an airtight connection with the filter 15, which guarantees the sterility of the device as a whole, while the air flowing from the plate-shaped component 6 through the central air exhaust channel 11 can be filtered through the filter 15 and released into the environment. However, guaranteeing the sterility of the blood product is the highest priority of the entire device.

Advantageously, the administration container 2 has a means of opening 18, such as a crack-and-break connection, which during administration makes it possible to open the administration container 2 easily before use without requiring any other aid or tool.

Through the channel 7 and the channels 8 connected to it and branching off to carry fluid, all of the administration containers 2 attached to the connectors 9 can be simultaneously and fully filled with the blood product 12 intended for use in patients.

Figure 2:
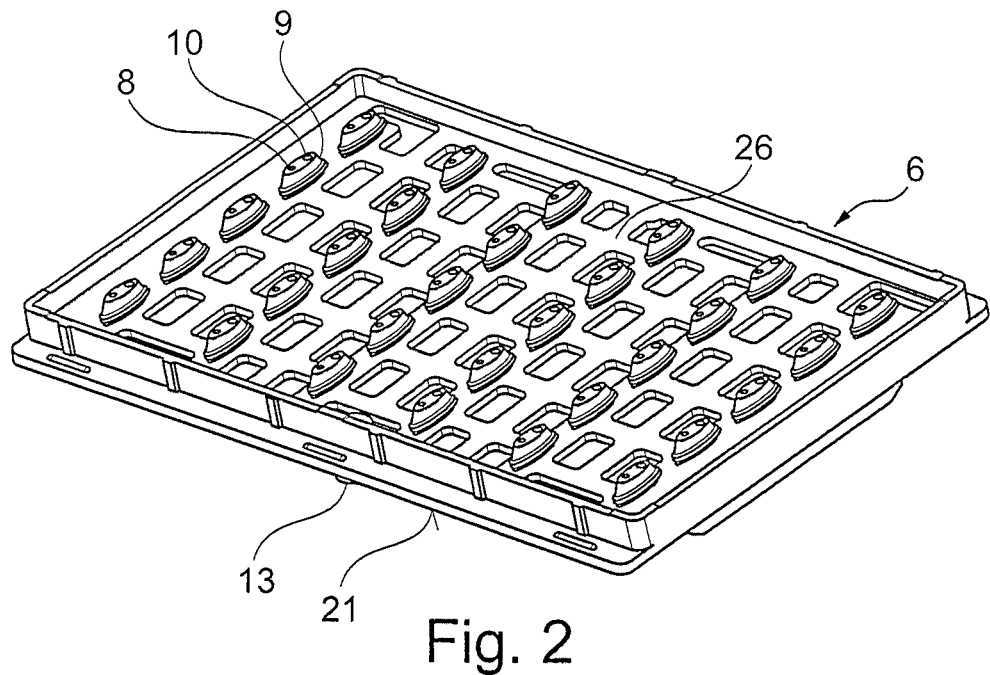

FIG. 2 shows the underside 26 of the plate-shaped component 6 with the individual connectors 9 arranged on it. Each connector 9 has a supply channel 8 and an air exhaust channel 10. In the example shown in FIG. 2, on its underside 26 the component 6 has thirty connectors 9 for connecting thirty administration containers 2. In addition, part of the connection 13 on the upper side 21 of the plate 6 can be seen. Additionally, rectangular recesses in the component 6 can be seen, which contribute to weight reduction. It also has offsets or guide rails on both long sides, with which the plate-shaped component is attached to a sealing and cutting device.

Figure 3:
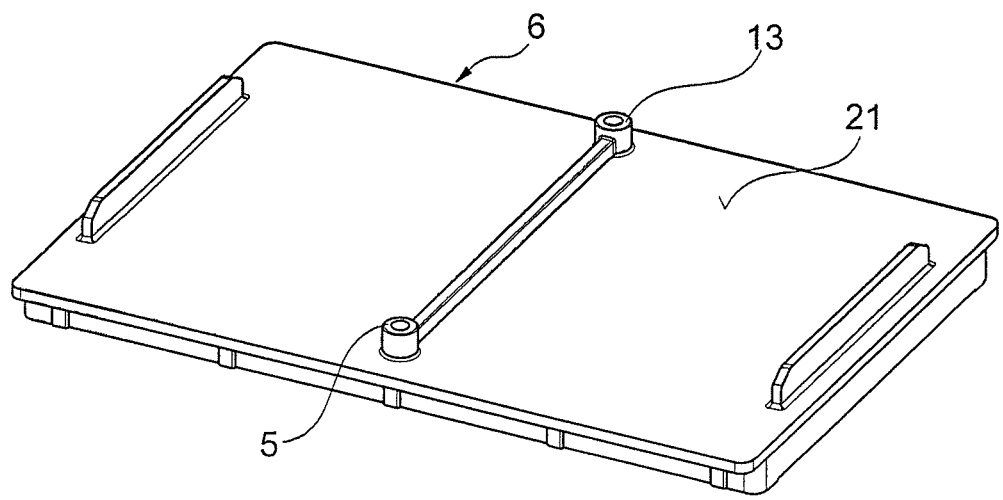

FIG. 3 shows a top view of the component 6, which on its top side 21 has a connection 5 for inflow of the blood product and a connection 13 for outflow of the excess air, wherein the latter is preferably connected to a filter.

Figure 4:
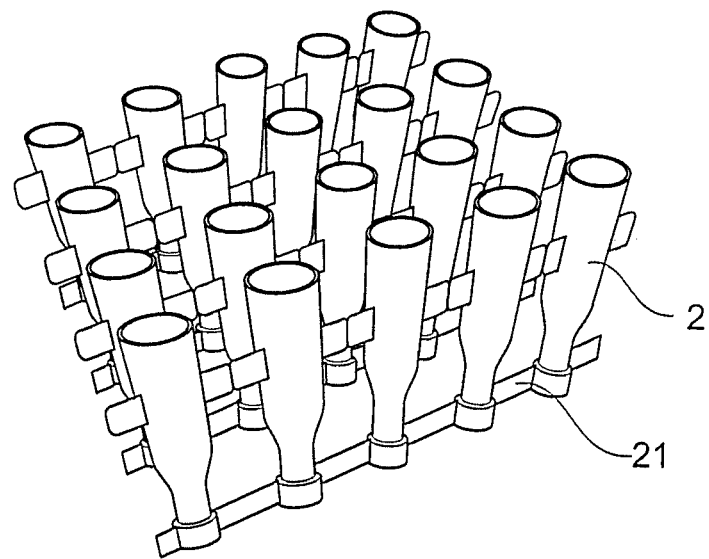

FIG. 4 shows the administration containers 2, which are already arranged on a surface corresponding to the distribution of the connectors 9. In an additional process step, the plate-shaped component with its connectors is laid on the arranged administration containers 2, and the containers are thereby attached to the connectors 9.

Figure 5:
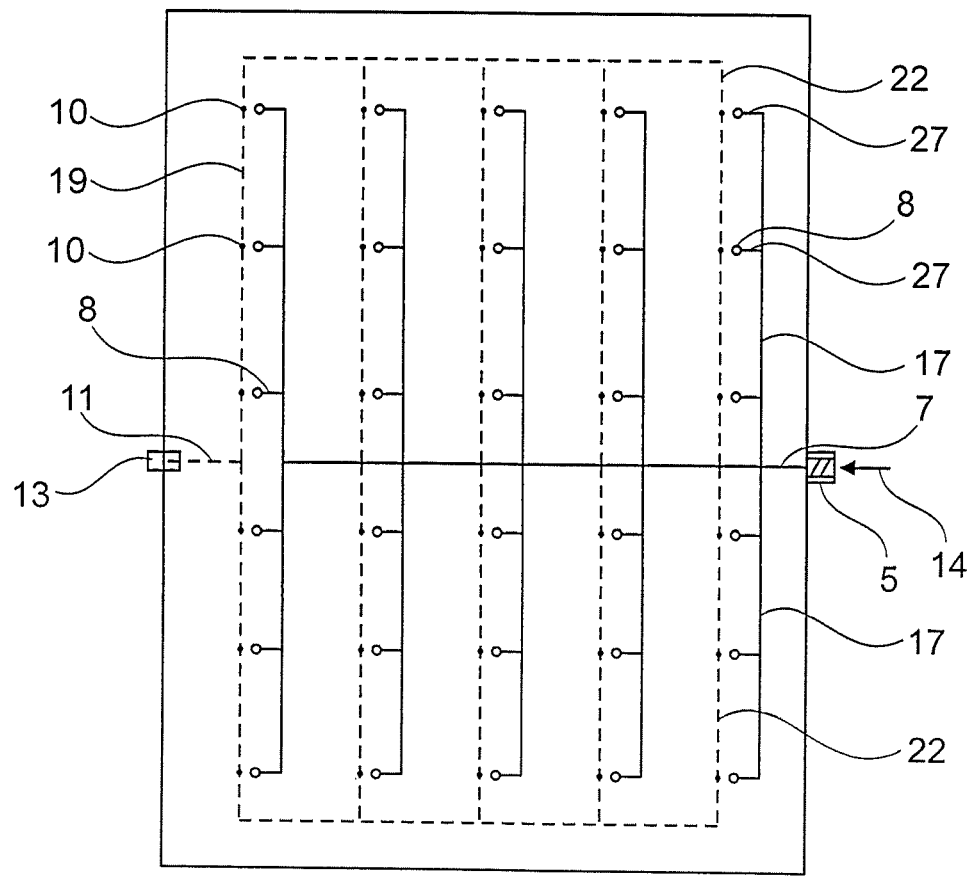

FIG. 5 shows the plate-shaped component 6 from above, with schematic representation of the channel paths. The plate shown here as an example has thirty supply channels 8 for filling the individual administration containers. Each supply channel 8 is connected through a connecting channel 27 to carry fluid to an adjacent channel 17, wherein each adjacent channel 17 is connected to carry fluid to the central channel 7. The central channel 7 in turn is filled with the blood product through the connection 5.

Next to each supply channel 8 there is an air exhaust channel 10, which has an airtight connection to an adjacent channel 22, wherein the adjacent channel 22 in turn has an airtight connection to the air exhaust channel 11. The air exhaust channel in turn has an airtight connection with the connection 13, to which a filter (not shown) is attached.

In order to achieve complete filling of all administration containers 2, a volume of the desired blood product is directed toward the administration containers 2 such that the fluid stream is sufficient to reach the outermost administration containers 2.

The device 1 fills by itself due to the hydrostatic drop or due to pressure applied to the receptacle 3 connected to the plate-shaped component 6. In this way, the blood product 12 flows through the feed line 4 into the channel 7 and from there into the adjacent channels 17 branching off from it. Branching off from the adjacent channels 17 are the connecting channels 27, the ends of which are connected to the administration containers 2 through the connectors 9. As the level of the blood product 12 increases in the administration containers 2, the air in them is pressed out through the air exhaust channels 10 into the supply channels 19 and directed into the channel 11, which is connected to the connection 13.

The filling process continues until all of the blood product is used up and all of the attached administration containers are filled. If necessary in order to better seal the containers, some unfilled space can be left in the containers.

DRAWING LEGEND

1 Device
2 Administration container
3 Receptacle
4 Feed line
5 Connection
6 Plate-shaped component
7 Supply channel (horizontal)
8 Supply channel (vertical)
9 Connector
10 Air exhaust channel
11 Air exhaust channel
12 Blood product
13 Connection
14 Direction arrow
15 Filter
16 (cover plate)
17 Adjacent channel
18 Means of opening
19 Supply channel
20 Cutting edge
21 Upper side
22 Adjacent channel
26 Lower side
27 Connecting channel

The invention claimed is:

1. A device for filling blood products into at least two administration containers, comprising at least one receptacle for dispensing the blood products into the device, a channel system is connected to carry fluid to the administration containers, and an air exhaust assembly wherein the device further comprises a plate-shaped component with channels of the channel system running through the plate-shaped component, and through the channels of the channel system the administration containers can be filled in parallel with equal volumes of the blood products, wherein the air exhaust assembly comprises a central exhaust channel and a plurality of air exhaust channels, wherein each air exhaust channel of the plurality of exhaust channels has an airtight connection to a supply channel, which in turn leads to the central air exhaust channel that carries air out of the plate-shaped component.

2. The device as in claim 1, wherein the administration containers-can be filled simultaneously and uniformly.

3. The device as in claim 1, wherein each channel of the channel system ends with a connector to which the administration containers are attached.

4. The device as in claim 3, wherein connectors are conical in shape.

5. The device as in claim 3, wherein the connector is arranged on an underside of the plate-shaped component.

6. The device as in claim 3, wherein the connector is connected to the supply channel and the air exhaust channel of the plurality of air exhaust channels.

7. The device as in claim 1, wherein in the plate-shaped component, a central supply channel distributes the blood products to multiple adjacent channels branching off from the central supply channel, which lead to the supply channels for connectors.

8. The device as in claim 1, wherein in the plate-shaped component, a central supply channel distributes the blood product to multiple adjacent channels branching off from the central supply channel, from which multiple adjacent channels further branch off and lead to the supply channels for connectors.

9. The device as in claim 1, wherein adjacent to each supply channel there is the air exhaust channel of the exhaust channels, which has an airtight connection to a connector.

10. The device as in claim 1, wherein at the end of the central air exhaust channel there is a connection to which a filter is attached to prevent any contamination of the blood products.

11. The device as in claim 1, wherein the supply channel has a change of the cross-section at connectors, in order to fill the fluid into the at least two administration containers under higher pressure and with increased velocity.

* * * * *